United States Patent [19]

Linares

[11] Patent Number: 4,639,538
[45] Date of Patent: Jan. 27, 1987

[54] DEODORIZED COMPOSITIONS BASED ON ORGANOTHIOPHOSPHORUS COMPOUNDS

[75] Inventor: Hubert Linares, Caluire, France

[73] Assignee: Rhone-Poulenc Agrochimie, Lyons, France

[21] Appl. No.: 608,097

[22] Filed: May 8, 1984

[30] Foreign Application Priority Data

May 10, 1983 [FR] France ................. 83 08020

[51] Int. Cl.⁴ .............................................. C07F 9/16
[52] U.S. Cl. .................................................... 558/71
[58] Field of Search ........................... 260/989; 558/71

[56] References Cited

U.S. PATENT DOCUMENTS 4,366,103 12/1982 Pearce et al. .................. 260/989

FOREIGN PATENT DOCUMENTS 2140270 1/1973 France .

OTHER PUBLICATIONS

Kharasch et al, "Chem. Abs.", vol. 50, (1956), 8507g.

Primary Examiner—Anton H. Sutto
Attorney, Agent, or Firm—Burns, Doane, Swecker & Mathis

[57] ABSTRACT

Deodorized composition based on an organothiophosphorus compound. It contains an effective quantity of styrene as a deodorizer. Composition with insecticidal or nematocidal activity.

9 Claims, No Drawings

DEODORIZED COMPOSITIONS BASED ON ORGANOTHIOPHOSPHORUS COMPOUNDS

The present invention relates to deodorised compositions based on organothiophosphorus compounds which are usually malodorous, and a process for deodorising these compounds.

It is known that many organothiophosphorus compounds are malodorous owing to their more or less extensive decomposition with a release of malodorous sulphur-containing products. It has already been proposed to add certain deodorisers such as, for example, linoleic acid, particularly for insecticidal and/or nematocidal active materials such as S,S-di-n-propopyl O-ethyl thiophosphate commonly referred to by the name of ethoprophos, when it is employed in the form of granules. However, such a solution does not resolve all the problems, particularly on account of the diversity of the solid carriers employed which promote the decomposition of the active material to various degrees, but also on account of storage and use conditions. In particular, a high temperature promotes the decomposition of the active material and consequently the release of malodorous sulphur-containing products.

The Applicant Company has now discovered that these compounds can be deodorised effectively by the addition of a suitable quantity of styrene.

More particularly, the invention relates to deodorised compositions based on usually malodorous organothiophosphorus compounds, which contain an effective quantity of styrene.

Malodorous organothiophosphorus products are understood in general to mean the compounds of the general formula:

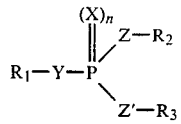

in which:

$R_1$ denotes a hydrogen atom, an alkyl radical containing from 1 to 8 carbon atoms, preferably from 1 to 4 carbon atoms, $R_2$ denotes an alkyl radical containing from 1 to 8 carbon atoms, preferably from 1 to 4 carbon atoms, $R_3$ denotes an alkyl radical containing from 1 to 8 carbon atoms, preferably from 1 to 4 carbon atoms, optionally substituted by a halogen atom, a carbonamide group itself optionally substituted by at least one alkyl or alkylthio or alkoxycarbonyl or a phenyl radical, phenyl substituted by 1 to 3 substituents chosen from the group comprising a halogen atom, an alkyl containing from 1 to 4 carbon atoms, and the nitro and cyano group.

X, Y, Z and Z', which may be identical or different, denote an oxygen atom or a sulphur atom, with n being an integer equal to 0 or 1, Y being moreover capable of being a direct bond between $R_1$ and the phosphorus atom, and at least one of X, Y, Z and Z' necessarily being a sulphur atom.

These products comprise organophosphates as well as organophosphonates. Among the organophosphates to which the invention applies in a particularly advantageous manner can be mentioned S,S-di-n-propyl O-ethyl phosphorodithioate or ethoprophos, and S-(1,2-dicarbethoxyethyl) O,O-dimethyldithiophosphate or malathion.

These products are present in the compositions according to the invention as an active material, most frequently an insecticide and/or a nematocide, at a concentration of 1 to 95% by weight.

The quantity of deodorising agent can vary extensively depending on the intended deodorising effect. In general, quantities of up to 50% by weight of the organothiophosphorus compound or compounds, and preferably between 5 and 40% by weight, are suitable.

The compositions according to the invention can additionally contain if need be other deodorisers such as linoleic acid, linolenic acid, mixtures of these acids, drying oils containing at least one of them, such as linseed oil and cottonseed oil.

Use can be made, moreover, of stabilising agents, particularly alkylene and polyalkylene glycols such as for example ethylene glycol, propylene glycol, butylene glycol, diethylene glycol, triethylene glycol and polyethylene glycol.

In the compositions according to the invention, the organothiophosphorus compounds additionally containing styrene as a deodoriser and, if need be, a stabiliser, are generally combined with carriers and surface-active agents.

In the present description the term "carrier" refers to an organic or inorganic substance, natural or synthetic, with which the active material is combined to facilitate its application to the plant, to seeds or to the soil. This carrier is therefore generally inert and it must be agriculturally acceptable, particularly on the plant being treated. The carrier can be solid (clays of the kaolin type, montmorillonite, attapulgite, sepiolite, natural or synthetic silicates, silica, talc, bentonite, diatomaceous earth, pyrophyllite, fuller's earth, gypsum, cottonseed flour and nut shell flour, pumice, resins, waxes, solid fertilisers, and the like) or liquid (water, alcohols, ketones, petroleum fractions, aromatic or paraffinic hydrocarbons, chlorinated hydrocarbons, liquefied gases, and the like).

The surface-active agent may be an emulsifying, dispersing or wetting agent of the ionic or nonionic type. Mention can be made for example of salts of polyacrylic acids, salts of lignosulphonic acids, salts of phenylsulphonic or naphthalenesulphonic acids, polycondensates of ethylene oxide with fatty alcohols or fatty acids or fatty amines, substituted phenols (particularly alkylphenols or arylphenols), salts of esters of sulphosuccinic acids, taurine derivatives (particularly alkyltaurates), and phosphoric esters of alcohols or of polycondensates of ethylene oxide with phenols. The presence of at least one surface-active agent is generally essential when the active material and/or the inert carrier are insoluble in water and when the carrier agent for the application is water.

The compositions according to the invention can take the form of various formulations, particularly solid or liquid such as wettable powders, granulates, emulsifiable concentrates and flowables.

The emulsifiable or soluble concentrates most frequently incorporate 10 to 80% of active ingredient, the emulsions or solutions ready for application containing, in their case, 0.01 to 20% of active ingredient. Besides the solvent, the emulsifiable concentrates can contain, when necessary, 2 to 20% of suitable additives such as stabilisers, surface-active agents, penetrating agents, corrosion inhibitors, colorants or adhesives.

Aqueous dispersions and emulsions, compositions obtained for example by diluting with water a wettable powder or an emulsifiable concentrate according to the invention are included in the general scope of the present invention. The emulsions can be of the water-in-oil or oil-in-water type and can have a thick consistency such as that of a "mayonnaise".

The granules intended to be applied on the soil are usually prepared so that they have dimensions of between 0.1 and 2 mm and can be produced by agglomeration or impregnation. In general, the granules contain 0.5 to 25% of active ingredient and 0 to 10% of additives such as stabilisers, slow-release modifying agents, binders and solvents.

The following examples illustrate deodorised compositions according to the invention together with the method for their preparation.

EXAMPLE 1

Styrene (20 parts), technical ethoprophos (105 parts) and propylene glycol (20 parts) are mixed at ambient temperature. The liquid mixture is then formulated with granular TOLSA sepiolite (855 parts) in a closed rotary drum. A granulate containing 10% by weight of ethoprophos is thus obtained which is free from bad odours of the mercaptan type.

EXAMPLE 2

3 deodorised granulates having the following composition by weight are prepared as in Example 1:

| | |
|---|---|
| technical ethoprophos (95%) | 105 |
| propylene glycol | 20 |
| styrene | 20 |
| Costa-Rica or Equador or Guatemala pumice | 855 |

EXAMPLE 3

A deodorised granulate having the following composition by weight is prepared as in Example 1:

| | |
|---|---|
| technical ethoprophos (95%) | 210 |
| propylene glycol | 20 |
| styrene | 20 |
| attapulgite | 750 |

EXAMPLE 4

A deodorised granulate having the following composition by weight is prepared as in Example 1:

| | |
|---|---|
| technical ethoprophos (95%) | 53 |
| propylene glycol | 20 |
| styrene | 10 |
| attapulgite | 917 |

EXAMPLE 5

A deodorised emulsifiable concentrate having the following composition by weight per 1 liter is prepared:

| | |
|---|---|
| technical ethoprophos (95%) | 756 |
| condensate of ethylene oxide (9-11 moles) with nonylphenol | 60 |
| calcium isopropylnaphthalenesulphonate | 60 |
| styrene | 40 |
| aromatic solvent | 104 |

I claim:

1. Deodorised compositions based on organothiophosphorus compounds which contain organothiophosphorus compounds of the formula:

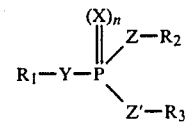

in which:
R₁ denotes a hydrogen atom, an alkyl radical containing from 1 to 8 carbon atoms, preferably from 1 to 4 carbon atoms,
R₂ denotes an alkyl radical containing from 1 to 8 carbon atoms, preferably from 2 to 4 carbon atoms,
R₃ denotes an alkyl radical containing from 1 to 8 carbon atoms, preferably from 1 to 4 carbon atoms, optionally substituted by a halogen atom, a carbonamide group itself optionally substituted by at least one alkyl or alkylthio or alkoxycarbonyl or a phenyl radical, phenyl substituted by 1 to 3 substituents chosen from the group comprising a halogen atom, an alkyl containing from 1 to 4 carbon atoms, and the nitro and cyano group.
X, Y, Z and Z', which may be identical or different, denote an oxygen atom or a sulphur atom, with n being an integer equal to 0 or 1, Y being moreover capable of being a direct bond between R₁ and the phosphorus atom, and at least one of X, Y, Z and Z' necessarily being a sulphur atom, and an effective quantity of styrene as a deodoriser.

2. Composition according to claim 1, in which the styrene is present at a concentration of 5 to 50% by weight of the organothiophosphorus compound.

3. Composition according to claim 2, in which the styrene is present at a concentration of 5 to 40% by weight of the organothiophosphorus compound.

4. Composition according to claim 1, in which the organothiophosphorus compound is S,S-di-n-propyl O-ethyl phosphorodithioate.

5. Composition according to claim 1, which additionally contains a stabiliser of the organothiophosphorus compound.

6. Composition according to claim 1, which is in the form of a granulate.

7. Composition according to claim 1, which is in the form of an emulsifiable concentrate.

8. Process for the manufacture of a composition according to claim 1, which comprises the addition, during the preparation of the composition, of an effective quantity of styrene as a deodoriser.

9. Composition according to claim 1 in which the organothiophosphorus compound is S-(1,2-dicarbethoxy-ethyl) O,O-dimethyldithiophosphate.

* * * * *